(12) United States Patent
Wong et al.

(10) Patent No.: US 9,675,608 B2
(45) Date of Patent: *Jun. 13, 2017

(54) IDENTIFICATION OF NATURAL SMALL-MOLECULES AMPK ACTIVATORS FOR TREATMENT OF CANCERS OR MULTIDRUG-RESISTANT CANCERS

(71) Applicant: Macau University of Science and Technology, Macau (CN)

(72) Inventors: Kam Wai Wong, Macau (CN); Yuen Kwan Law, Macau (CN); Liang Liu, Macau (CN)

(73) Assignee: Macau University of Science and Technology, Macau (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/925,962

(22) Filed: Oct. 28, 2015

(65) Prior Publication Data

US 2017/0056390 A1    Mar. 2, 2017

Related U.S. Application Data

(60) Provisional application No. 62/210,441, filed on Aug. 26, 2015.

(51) Int. Cl.
*A61K 31/44* (2006.01)
*A61K 31/4745* (2006.01)

(52) U.S. Cl.
CPC .............. *A61K 31/4745* (2013.01)

(58) Field of Classification Search
USPC ......................................................... 514/280
See application file for complete search history.

(56) References Cited

U.S. PATENT DOCUMENTS 6,617,335 B1 * 9/2003 Wang .................. C07D 491/18
                                                              514/308
7,799,782 B2 * 9/2010 Munson ............... C07D 231/56
                                                              514/234.5

FOREIGN PATENT DOCUMENTS

WO      WO92/18131     * 10/1992

OTHER PUBLICATIONS

Van Dyke's CAS: 118: 52417, 1993.*
Xu et al. CAS: 113: 126166, 1990.*
Mihaylova, M.M. & Shaw, R.J., The AMPK signalling pathway coordinates cell growth, autophagy and metabolism. Nat Cell Biol 2011, vol. 13, No. 9, p. 1016-23.
Chan, E.Y.W., Kir, S. & Tooze, S.A., siRNA screening of the kinome identifies ULK1 as a multidomain modulator of autophagy. J Biol Chem 2007, vol. 282, No. 35, p. 25464-74.
Ganley, I.G. et al., ULK1.ATG13.FIP200 complex mediates mTOR signaling and is essential for autophagy. J Biol Chem 2009, vol. 284, No. 18, p. 12297-305.
Mizushima, N., The role of the Atg1/ULK1 complex in autophagy regulation. Curr Opin Cell Biol 2010, 22:132-9.
Kim, J., Kundu, M., Viollet, B. & Guan, K.L., AMPK and mTOR regulate autophagy through direct phosphorylation of Ulk1. Nat Cell Biol 2011, 13(2):132-141.
Xiao, B. et al., Structural basis of AMPK regulation by small molecule activators. Nat Commun 2013, 4:3017.
Steinberg, G.R. & Kemp, B.E., AMPK in Health and Disease, Physiol Rev 2009, vol. 89, p. 1025-78.
Yang, Z.J., Chee, C.E., Huang, S. & Sinicrope, F.A., The role of autophagy in cancer: therapeutic implications. Mol Cancer Ther 2011, 10(9):1533-41.
Law, B.Y.K. et al., Natural small-molecule enhancers of autophagy induce autophagic cell death in apoptosis-defective cells. Sci Rep 2014, 4:5510.
Wang, G. & Lemos, J.R., Tetrandrine: a new ligand to block voltage-dependent Ca2+ and Ca(+)-activated K+ channels. Life Sci 1995, vol. 56, No. 5, p. 295-306.
Leung, Y.M., Kwan, C.Y. & Loh, T.T., Dual effects of tetrandrine on cytosolic calcium in human leukaemic HL-60 cells: intracellular calcium release and calcium entry blockade. Br J Pharmacol 1994, 113, 767-74.
Low, A.M. et al., Plant alkaloids, tetrandrine and hernandezine, inhibit calcium-depletion stimulated calcium entry in human and bovine endothelial cells. Life Sci 1996, vol. 58, No. 25, p. 2327-35.
Xu, C.X., Lin, L., Sun, R.H., Liu, X. & Han, R., Anti-tumor effect of hernandezine and other components extracted from Thalictrum glandulosissimum, Acta Pharmaceutica Sinica 1990, 25(5):330-5.
Mizushima, N. & Klionsky, D.J., Protein turnover via autophagy: implications for metabolism. Annu Rev Nutr 2007, vol. 27, p. 19-40.
Xiao, K. et al., Curcumin induces autophagy via activating the AMPK signaling pathway in lung adenocarcinoma cells. J Pharmacol Sci 2013, 123, 102-9.

* cited by examiner

*Primary Examiner* — Rei-Tsang Shiao
(74) *Attorney, Agent, or Firm* — Eagle IP Limited; Jacqueline C. Lui (57) ABSTRACT

The present invention discloses a method of treating cancer and/or multidrug-resistant cancer, comprising administering an effective amount of hernandezine or thalidezine. A pharmaceutical composition comprising hernandezine or thalidezine admixed with a pharmaceutical carrier for treating cancers and/or multidrug-resistant cancer is also disclosed.

**9 Claims, 10 Drawing Sheets
(6 of 10 Drawing Sheet(s) Filed in Color)**

IDENTIFICATION OF NATURAL SMALL-MOLECULES AMPK ACTIVATORS FOR TREATMENT OF CANCERS OR MULTIDRUG-RESISTANT CANCERS

CROSS-REFERENCE TO RELATED APPLICATION

This application claims benefit under 35 U.S.C. §119(e) of U.S. Provisional Application having Ser. No. 62/210,441 filed 26 Aug. 2015, which is hereby incorporated by reference herein in its entirety.

FIELD OF INVENTION

This invention relates to a novel treatment for treating cancers or multidrug-resistant cancers, in particular, a novel treatment involving the use of an AMPK activator, hernandezine or thalidezine.

BACKGROUND OF INVENTION

AMP activated protein kinase (AMPK), which maintains normal energy balance by regulating cellular metabolisms in an AMP/ADP ratio-dependent manner, is critically responsible for the proper mechanistic modulation of autophagy. During cellular starvation, AMPK induces autophagy by phosphorylating Ulk1, the mammalian counterpart of ATG1, at Ser 317 and 777. Molecular studies demonstrated that Ulk1 together with another mammalian ATG1 homolog Ulk2 interacted with mATG13 and FIP200 (mammalian homologues of ATG13 and ATG17) to form complex and regulate the autophagic machinery. Extensive genetic studies using yeast models have also suggested the inductive role of ATG1 kinase in autophagy. Conversely, under nutrient-rich conditions, the activation of mTOR prevents the phosphorylation of Ulk1 activation through Ser 757, which finally inhibits the Ulk1-AMPK regulated induction of autophagy. Besides, AMPK stimulates autophagy through the inhibition of mTORC1, which is the key regulator of growth factor and nutrient signals transduction.

In fact, autophagy may play its anti-cancer role by preventing accumulation of damaged proteins and organelles which leads to the progression of tumor growth, or via the induction of autophagic cell death. However, some studies show that AMPK activator may also stimulate cell grow under some circumstances. Therefore, identification of novel AMPK activator for the induction of autophagy has been a new approach for new cancer drug discovery.

SUMMARY OF INVENTION

In the light of the foregoing background, it is an object of the present invention to provide an alternate AMPK activator in treating cancers.

Accordingly, in one aspect of the present invention, a method of treating multidrug-resistant cancer including administering an effective amount of hernandezine or thalidezine is provided.

In an exemplary embodiment, the multidrug-resistant cancer is colon cancer. In another exemplary embodiment, the colon cancer that is resistant to taxol, etoposide, doxorubicin, cisplatin, staurosporine, or any combination thereof.

In another exemplary embodiment, the multidrug-resistant cancer is resistant to taxol, etoposide, doxorubicin, cisplatin, staurosporine, or any combination thereof.

The present invention, in another aspect, is a method of treating cancer including administering an effective amount of thalidezine, in which the cancer is lung cancer, liver cancer, breast cancer, cervical cancer, prostate cancer or colon cancer.

In another exemplary embodiment, the multidrug-resistant cancer is p53 deficient multidrug-resistant cancer. In yet another exemplary embodiment, the p53 deficient multidrug-resistant cancer is p53 deficient multidrug-resistant colon cancer.

In one exemplary embodiment, the p53 deficient multidrug-resistant colon cancer is resistant to taxol, etoposide, doxorubicin, cisplatin, staurosporine, or any combination thereof.

In yet another aspect of this invention, a method of treating colon cancer including administering an effective amount of hernandezine is provided.

In an exemplary embodiment of the present invention, the colon cancer is multidrug-resistant cancer.

In another aspect, a pharmaceutical composition for treating cancer including an alkaloid and a pharmaceutical carrier is provided, in which the alkaloid is hernandezine or thalidezine.

In an exemplary embodiment, the multidrug-resistant cancer is colon cancer. In another exemplary embodiment, the colon cancer that is resistant to taxol, etoposide, doxorubicin, cisplatin, staurosporine, or any combination thereof.

In another exemplary embodiment, the multidrug-resistant cancer is resistant to taxol, etoposide, doxorubicin, cisplatin, staurosporine, or any combination thereof.

According to another aspect of the present invention, a method of treating multidrug-resistant cancer including administering an effective amount of thalidezine is provided, in which the cancer is lung cancer, liver cancer, breast cancer, cervical cancer, prostate cancer or colon cancer.

In one exemplary embodiment, the multidrug-resistant cancer is p53 deficient multidrug-resistant cancer. In another exemplary embodiment, the p53 deficient multidrug-resistant cancer is p53 deficient multidrug-resistant colon cancer.

In yet another exemplary embodiment, the p53 deficient multidrug-resistant colon cancer is resistant to taxol, etoposide, doxorubicin, cisplatin, staurosporine, or any combination thereof.

In yet another aspect of this invention, a pharmaceutical composition for multidrug-resistant cancer including an alkaloid and a pharmaceutical carrier, in which the alkaloid is hernandezine or thalidezine is provided.

In an exemplary embodiment, the multidrug-resistant cancer is colon cancer. In another exemplary embodiment, the colon cancer that is resistant to taxol, etoposide, doxorubicin, cisplatin, staurosporine, or any combination thereof.

In another exemplary embodiment, the multidrug-resistant cancer is resistant to taxol, etoposide, doxorubicin, cisplatin, staurosporine, or any combination thereof.

In another aspect, a pharmaceutical composition for treating cancer including thalidezine and a pharmaceutical carrier is provided, in which the cancer is lung cancer, liver cancer, breast cancer, cervical cancer or prostate cancer.

In another exemplary embodiment, the multidrug-resistant cancer is p53 deficient multidrug-resistant cancer. In yet another exemplary embodiment, the p53 deficient multidrug-resistant cancer is p53 deficient multidrug-resistant colon cancer.

In one exemplary embodiment, the p53 deficient multidrug-resistant colon cancer is resistant to taxol, etoposide, doxorubicin, cisplatin, staurosporine, or any combination thereof.

Another aspect of the invention provides a pharmaceutical composition for treating colon cancer including hernandezine and a pharmaceutical carrier.

In an exemplary embodiment of the present invention, the colon cancer is multidrug-resistant cancer.

BRIEF DESCRIPTION OF FIGURES

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

As used herein and in the claims, "comprising" means including the following elements but not excluding others.

Recently, some small molecule AMPK activators have been identified as potential therapeutic agent for metabolic diseases or cancers. Natural compounds such as α-Lipoic acid, polyphenols (resveratrol) and isoquinoline alkaloid (berberine); small molecule activators such as A-769662, metformin and thiazolidinediones (TZDs) could activate AMPK in a variety of cell types.

Hernandezine, as represented by Formula (I) below, is an alkaloid isolated from Chinese medicinal herb that has long been used for treating hypertension and angina pectoris. Although the molecular mechanisms and targets of hernandezine remained unclear, there was report suggesting that hernandezine blocks the influx of calcium via non selective cation channels in HL-60 cells. Further study showed that the calcium influx triggered by depletion of internal calcium storage was blocked by hernandezine.

(I)

Similar to hernandezine, another alkaloid compound thalidezine as represented by Formula (II) below, which was isolated from the same herb (*T. glandulosissimum*), was only reported to arrest cell-cycle in G1 phase of mouse L1210 cells. Nevertheless, the biological function and molecular target of thalidezine are not known. In the present study, the inventors further depicted that hernandezine and thalidezine are the novel AMPK activators, that could able to induce cell death in cancer cells and drug-resistant cancer cells via direct activation of AMPK kinase.

(II)

Example 1

Demonstration of Specific Cytotoxicity by Hernandezine and Thalidezine on Various Types of Cancer Cells

1.1 Cell Culture and Cytotoxicity Assay

Hernandezine and thalidezine are dissolved in DMSO at a final concentration of 100 mmol/L and stored at −20° C. Cytotoxicity is assessed using the 3-(4,5-dimethylthiazol-2-yl)-2,5-diphenyltetrazolium bromide assay. 4000 cells of HeLa (cervical cancer), A549 (lung cancer), MCF-7 (breast cancer), PC3 (prostate cancer), HepG2 (liver cancer), Hep3B (liver cancer) and H1299 (lung cancer) cells and LO2 normal hepatocytes are seeded on 96-well plates per well. After overnight pre-incubation, the cells are exposed to different concentrations of hernandezine or thalidezine (0.039-100 μmol/L) for 3 days. Subsequently, 10 μL of MTT reagents is added to each well and incubated at 37° C. for 4 hours followed by the addition of 100 μL solubilization buffer (10% SDS in 0.01 mol/L HCl) and overnight incubation. Absorbance at 585 nm is determined from each well on the next day. The percentage of cell viability is calculated using the following formula: Cell viability (%)=Cells number treated/Cells number DMSO control×100. Data is obtained from three independent experiments.

1.2 Results

To clarify the anti-tumor effect of hernandezine and thalidezine, a panel of cancer cells, including HeLa, A549, MCF-7, PC3, HepG2, Hep3B and H1299 were adopted in the cytotoxicity assay, whereas the normal human hepatocytes, LO2, were used for comparison. As shown in Table 1, potent cytotoxic effects towards all of the tested cancer cells types were observed in hernandezine treatment, especially on A549 lung cancer cells (mean $IC_{50}$, 7.59 μM), HepG2 liver cancer cells (mean $IC_{50}$, 7.42 μM), Hep3B liver cancer cells (mean $IC_{50}$, 6.71 μM) and H1299 lung cancer cells (mean $IC_{50}$, 6.74 μM). In contrast, hernandezine exhibited relative low cytotoxicity towards normal liver hepatocytes, LO2 (mean $IC_{50}$, 65.1 μM).

Further, thalidezine indicated potent cytotoxic effects towards all of the tested cancer cells, especially on A549 lung cancer cells (mean $IC_{50}$, 7.47 μM), MCF-7 breast cancer cells (mean $IC_{50}$, 9.9 μM), HepG2 liver cancer cells (mean $IC_{50}$, 10.6 μM), Hep3B liver cancer cells (mean $IC_{50}$, 8.07 μM) and H1299 lung cancer cells (mean $IC_{50}$, 7.47 μM). Concomitantly, thalidezine exhibited relative low cytotoxicity toward LO2 normal liver hepatocytes (mean $IC_{50}$, 88.4 μM).

In summary, both hernandezine and thalidezine show specific cytotoxic effect towards cancer cells.

TABLE 1

Cytotoxicity analysis of hernandezine and thalidezine in a panel of cancer and normal cells

| Cell types | Hernandezine (Mean μM) | Thalidezine (Mean μM) |
|---|---|---|
| HeLa (Cervical) | 14.8 | 14.8 |
| A549 (Lung) | 7.59 | 7.47 |
| MCF-7 (Breast) | 14 | 9.9 |
| PC3 (Prostate) | 11.4 | 13.1 |
| HepG2 (Liver) | 7.42 | 10.6 |
| Hep3B (Liver) | 6.71 | 8.07 |
| H 1299 (Lung) | 6.74 | 7.47 |
| LO2 (Liver-normal) | 65.1 | 88.4 |

Example 2

Direct Activation of AMPK Kinase Activity by Hernandezine and Thalidezine

2.1 AMPK Kinase Assay:

AMPK kinase assay was performed using CycLex® AMPK Kinase Assay Kit (MBL, Japan) according to manufacturing instructions. In brief, 0.2 ng of AMPK (α1/β1γ1) active enzyme (CycLex Co., Ltd.) was incubated in well with 10× of hernandezine or thalidezine (50 & 100 μM) or 10× of positive control, AMP (100 μM) in kinase assay buffer (50 μM ATP & 10 mM DTT) at 30° C. for 20 minutes. The reaction was then stopped by washing with five times of Wash buffer. Then, anti-Phospho-mouse IRS-1 5789 monoclonal antibody was added to each well at room temperature for 30 minutes. After washing with Wash buffer for five times, HRP-conjugated anti-mouse IgG was added to each well at room temperature for 30 minutes. After washing with Wash buffer, the TMB Substrate Reagent was incubated in wells at room temperature for 5-15 minutes. Stop solution was added to each well before absorbance 450/550 nm measurement was taken.

2.2 Results

Figure 1:
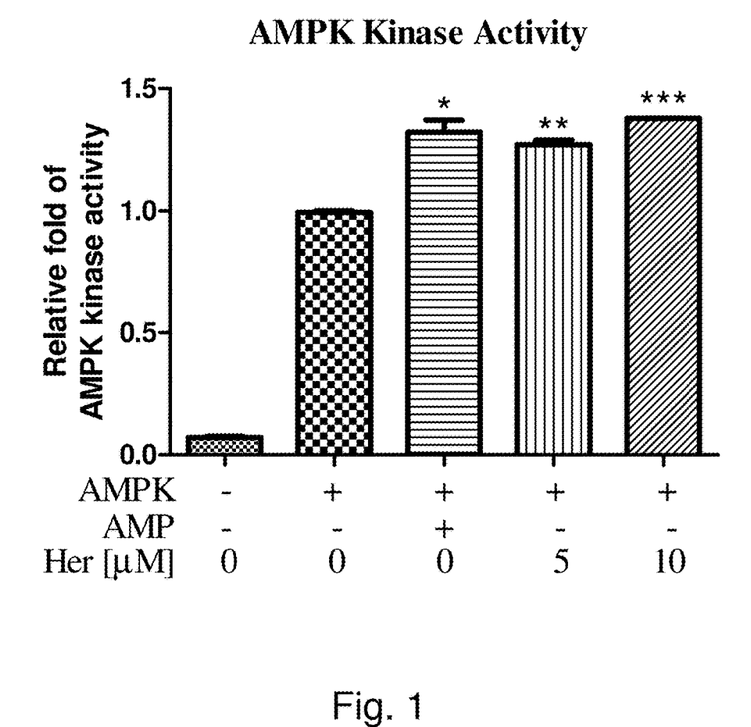
FIG. 1 is the bar chart quantitation for demonstrating the activation of AMPK kinase activity in response to hernandezine (Her) treatment, in which AMP is one of the well-known AMPK activators.
Figure 2:
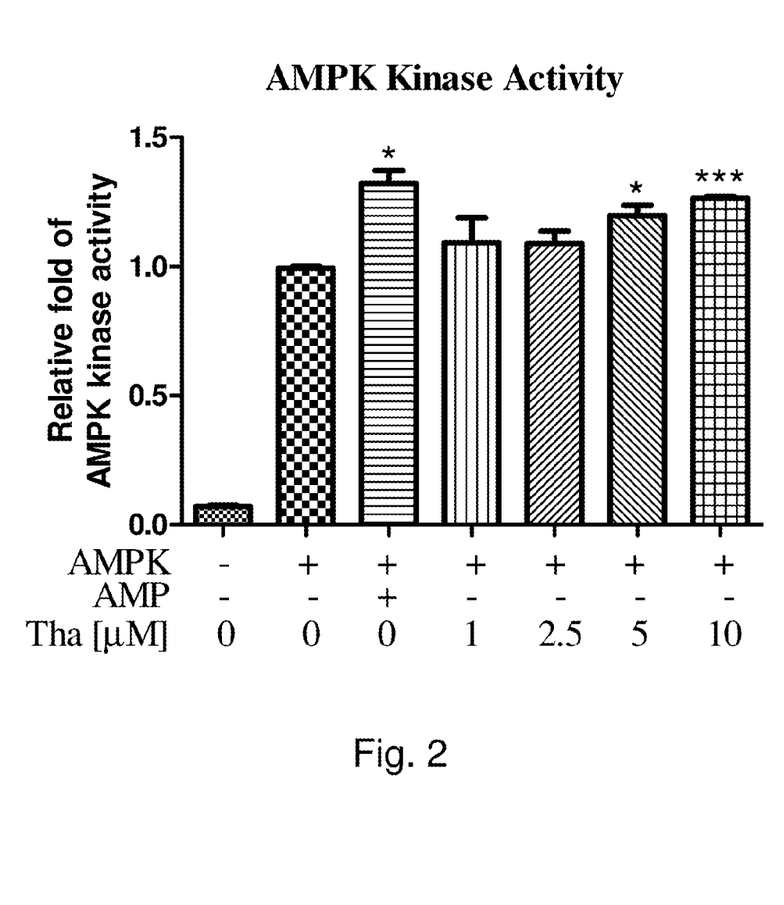
FIG. 2 is the bar chart quantitation for demonstrating the activation of AMPK kinase activity in response to thalidezine (Tha) treatment, in which AMP is one of the well-known AMPK activators.

To demonstrate the effect of hernandezine and thalidezine on AMPK activation, a cell free AMPK kinase assay was adopted in this study. AMPK kinase assay revealed that both hernandezine and thalidezine could dose-dependently activate the AMPK kinase activity as compared to AMPK enzyme alone, whereas the positive control AMP also increased the AMPK kinase activity as well as shown in FIGS. 1 and 2. These findings suggest that the alkaloid compounds hernandezine and thalidezine can directly activate AMPK kinase.

Example 3

Activation of AMPK-mTOR Signaling Pathways by Hernandezine and Thalidezine

3.1 Detection of mTOR Signaling Marker Proteins

HeLa cells treated with indicated time and concentrations of hernandezine or thalidezine were harvested and lysed in RIPA buffer (Cell Signaling). The cell lysates were then resolved by SDS-PAGE. After electrophoresis, the proteins from SDS-PAGE were transferred to nitrocellulose membrane which was then blocked with 5% non-fat dried milk for 60 minutes. The membrane was then incubated with P-p70S6K, p70S6K, P-AMPK, AMPK, P-Acc and actin primary antibodies (1:1000) in TBST overnight at 4° C. respectively. After that, the membrane was further incubated with HRP-conjugated secondary antibodies for 60 minutes. Finally, protein bands were visualized by using the ECL Western Blotting Detection Reagents (Invitrogen).

3.2 Results

Figure 3A:
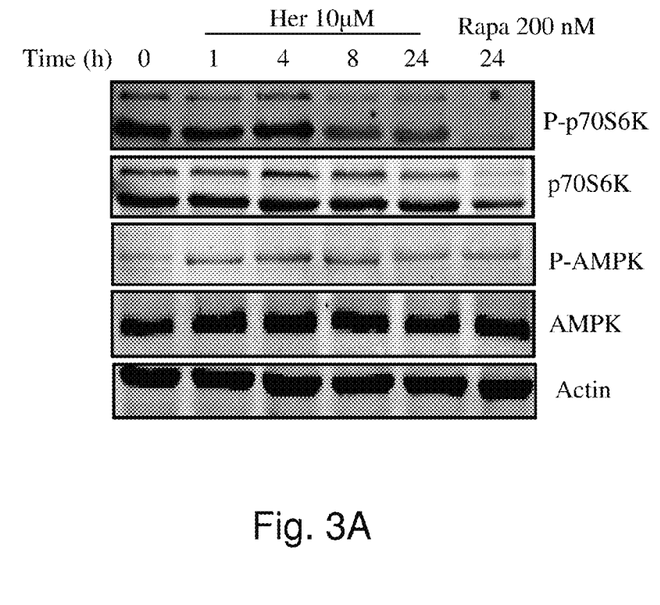
FIG. 3A is the Western blot to show the effect of hernandezine (Her) on AMPK-mTOR signaling pathways, in which Rapamycin (Rapa) is the positive control.
Figure 3B:
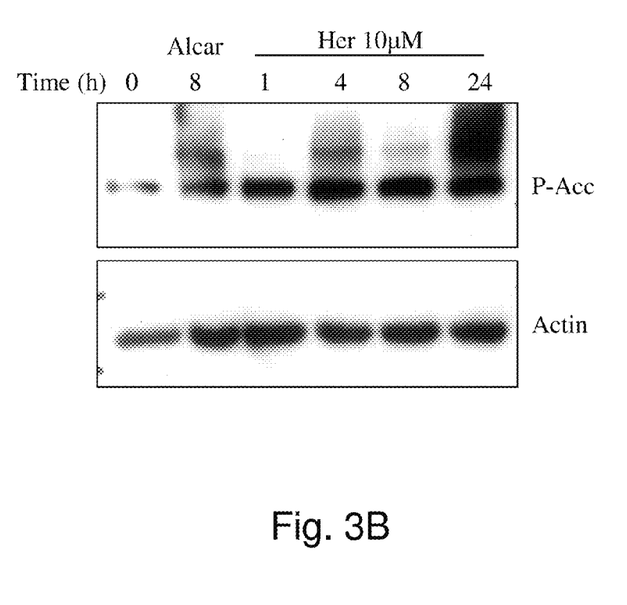
FIG. 3B is the Western blot to show the effect of hernandezine (Her) on the activation of AMPK substrate, Acc, in which Alcar is the positive control.
Figure 4:
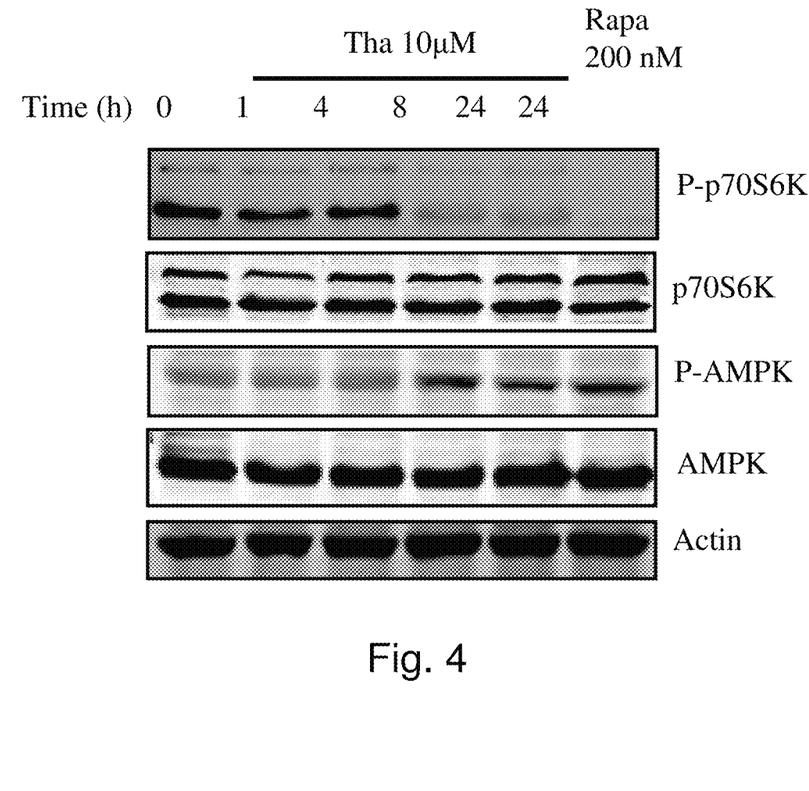
FIG. 4 is the Western blot to show the effect of thalidezine (Tha) on AMPK-mTOR signaling pathways, in which Rapamycin (Rapa) is the positive control.

AMPK is a sensor of cellular energy status that is activated under high intracellular AMP conditions such as hypoxia or nutrient deprivation, thereby induces autophagy via the AMPK-mTOR-dependent pathway. Phosphorylation of AMPK and its downstream target Acetyl-Coenzyme A Carboxylase (ACC) are required for small-molecule mediated autophagy. In the current study, AMPK phosphorylation was increased in response to hernandezine or thalidezine treatment as demonstrated by the Western blot results as shown in FIGS. 3A and 4. It was then accompanied by a reduction in phosphorylated p70S6K, a downstream target of mTOR (FIGS. 3A and 4), whereas ACC, the direct downstream target of AMPK was concomitantly phosphorylated upon hernandezine treatment as shown in FIG. 3B.

Example 4

Abolishing the Hernandezine-Mediated or Thalidezine-Mediated Cell Death in HeLa Cancer Cells by Supplement of Glycolytic Intermediate 4.1 Cell Culture and Flow Cytometry Analysis Cell viability was measured using an annexin V staining kit (BD Biosciences, San Jose, Calif., USA). Briefly, HeLa cells were treated with 10 µM of hernandezine or thalidezine for 24 h in the presence or absence of glycolytic intermediate, methyl pyruvate (MP). Cells were then harvested and analyzed by multiparametric flow cytometry using FITC-Annexin V and Propidium iodide staining (BD Biosciences, San Jose, Calif., USA) according to the manufacturer's instructions. Flow cytometry was then carried out using a FACSCalibur flow cytometer (BD Biosciences, San Jose, Calif., USA). Data acquisition and analysis were performed with CellQuest (BD Biosciences, San Jose, Calif., USA). Data was obtained from three independent experiments.

4.2 Results

Figure 5A:
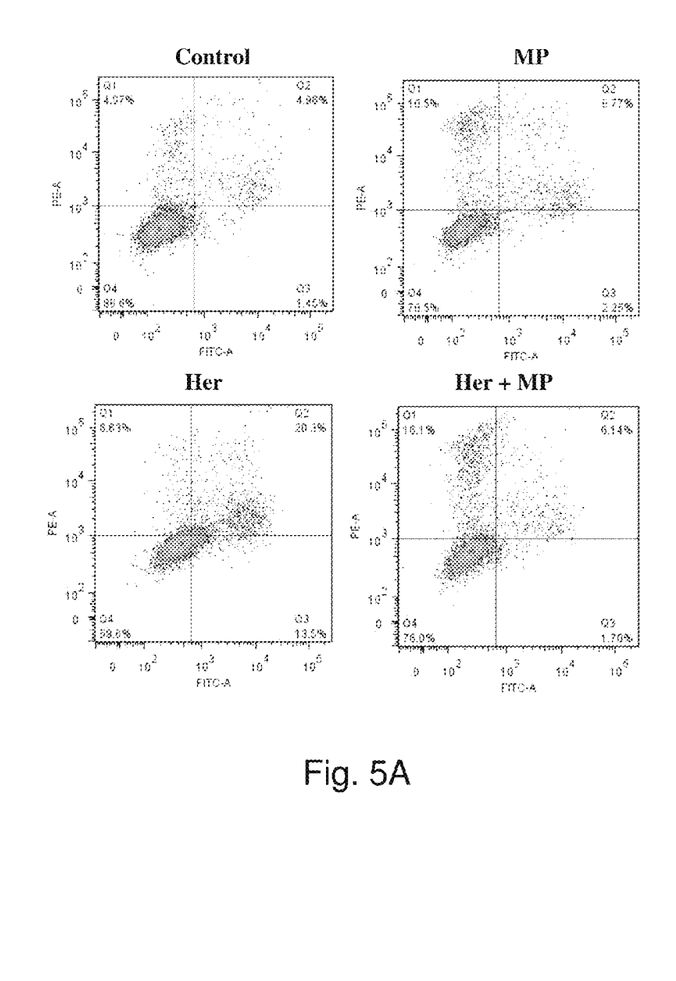
FIG. 5A is the flow cytometry analysis of cell death (annexin V) in response to hernandezine (Her) treatment with or without glycolytic supplement, methyl-pyruvate (MP), in HeLa cancer cells.
Figure 5B:
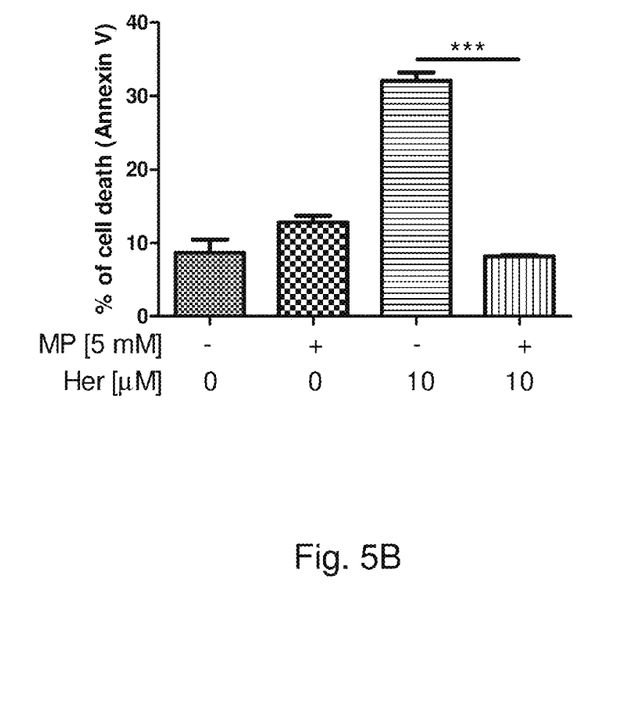
FIG. 5B is the bar chart quantitation for showing the percentage of cell death in response to hernandezine (Her) treatment with or without glycolytic supplement, methyl-pyruvate (MP), in HeLa cancer cells.
Figure 6A:
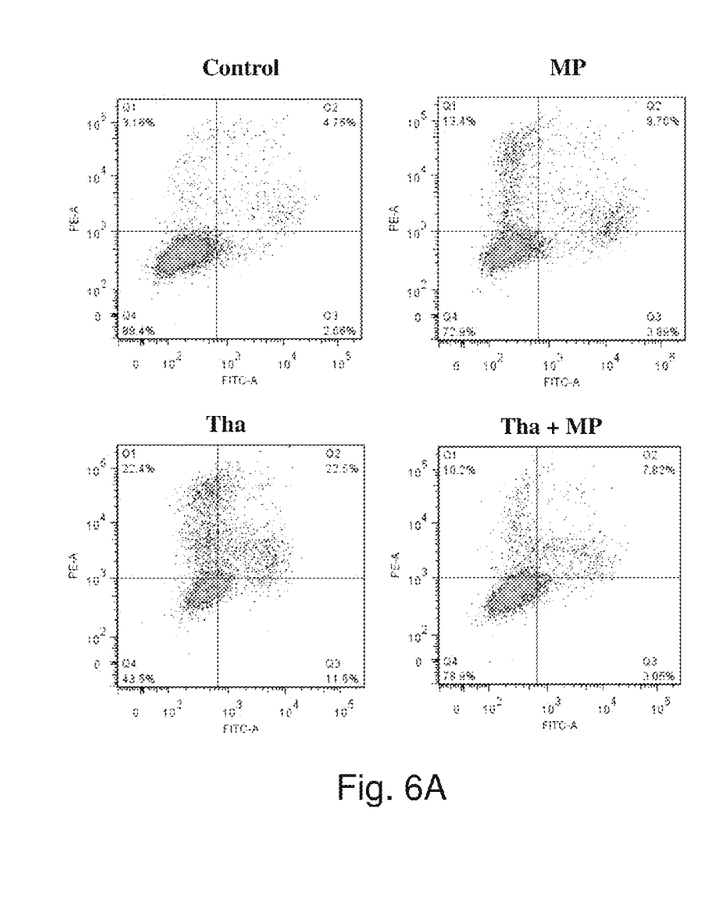
FIG. 6A is the flow cytometry analysis of cell death (annexin V) in response to thalidezine (Tha) treatment with or without glycolytic supplement, methyl-pyruvate (MP), in HeLa cancer cells.
Figure 6B:
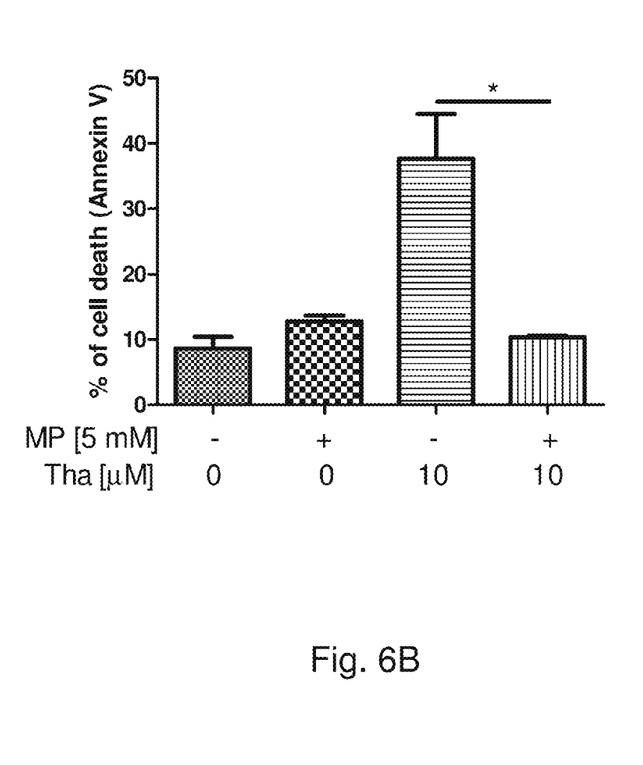
FIG. 6B is the bar chart quantitation for showing the percentage of cell death in response to thalidezine (Tha) treatment with or without glycolytic supplement, methyl-pyruvate (MP), in HeLa cancer cells.
Figure 7A:
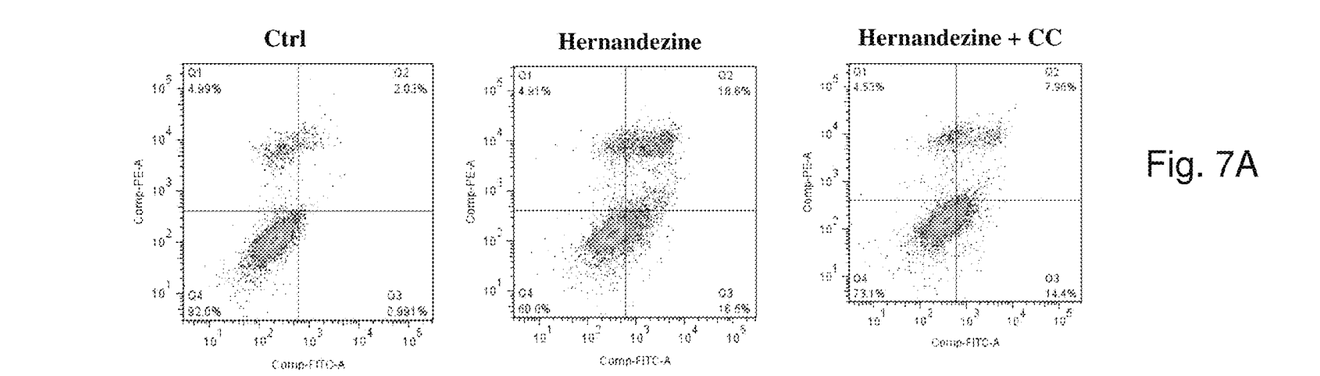
FIG. 7A is the flow cytometry analysis of cell death (annexin V) in response to hernandezine (Her) treatment with or without AMPK inhibitor, compound C (CC), in Bax-Bak DKO apoptosis-resistant MEF cells.
Figure 7B:
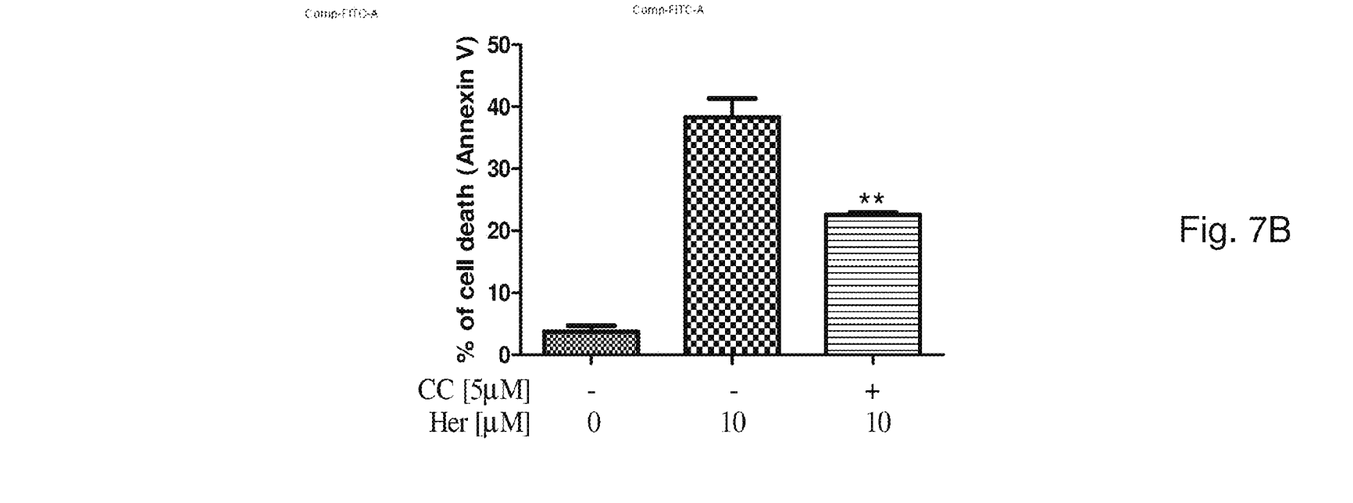
FIG. 7B is the bar chart quantitation for showing the percentage of cell death in response to hernandezine (Her) treatment with or without AMPK inhibitor, compound C (CC), in Bax-Bak DKO apoptosis-resistant MEF cells.
Figure 8A:
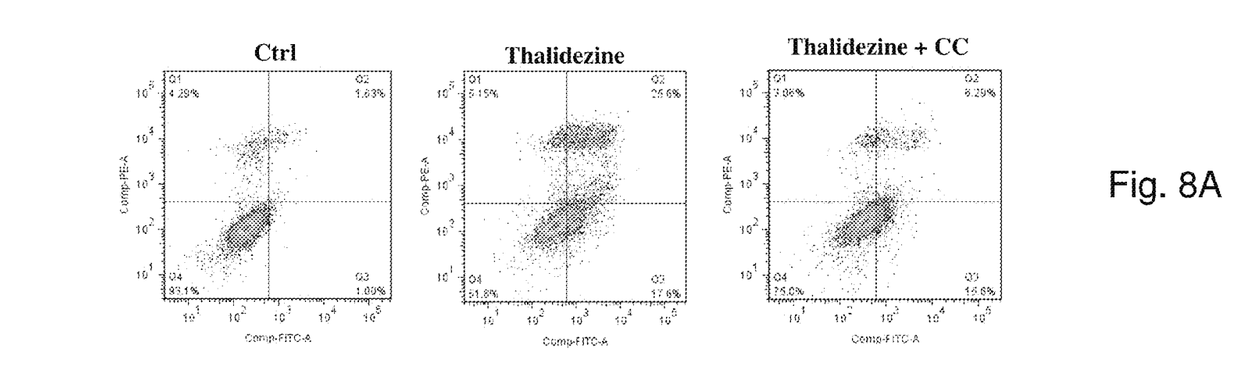
FIG. 8A is the flow cytometry analysis of cell death (annexin V) in response to thalidezine (Tha) treatment with or without AMPK inhibitor, compound C (CC), in Bax-Bak DKO apoptosis-resistant MEF cells.
Figure 8B:
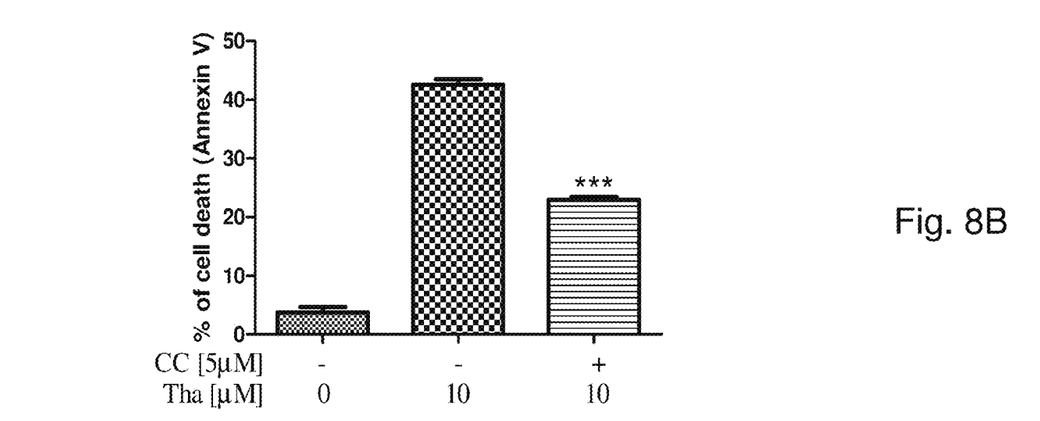
FIG. 8B is the bar chart quantitation for showing the percentage of cell death in response to thalidezine (Tha) treatment with or without AMPK inhibitor, compound C (CC), in Bax-Bak DKO apoptosis-resistant MEF cells.

AMPK is a sensor of cellular energy status, activation of AMPK may affect the cell energy level. Since both alkaloid compounds have shown direct activation of AMPK signaling, the inventors therefore determined whether the alkaloid compounds-mediated cell death on cancer cells is related to cell energy metabolism. As shown in FIGS. 5A, 5B, 6A and 6B, HeLa cells treated with either hernandezine or thalidezine have demonstrated significant cell death with annexin V signal, whereas addition of the glycolytic intermediate, methyl pyruvate (MP), alone showed basal level of cell death as compared to the medium control as shown in FIGS. 5B and 6B. However, supplementation of methyl pyruvate was capable of suppressing hernandezine-mediated or thalidezine-mediated cell death as shown in FIGS. 5A, 5B, 6A and 6B, suggesting that energy depletion was involved in both hernandezine and thalidezine-induced cell death.

Example 5

Abolishing the Hernandezine-Mediated or Thalidezine-Mediated Cell Death in Bax-Bak DKO Apoptosis-Resistant MEF Cells by AMPK Inhibitor, Compound C 5.1 Cell Culture and Flow Cytometry Analysis Cell viability was measured using an annexin V staining kit (BD Biosciences, San Jose, Calif., USA). Briefly, Bax-Bak DKO apoptosis-resistant MEF cells were treated with 10 µM of hernandezine or thalidezine for 24 h in the presence or absence of AMPK inhibitor, compound C (CC). Cells were then harvested and analyzed by multiparametric flow cytometry using FITC-Annexin V and Propidium iodide staining (BD Biosciences, San Jose, Calif., USA) according to the manufacturer's instructions. Flow cytometry was then carried out using a FACSCalibur flow cytometer (BD Biosciences, San Jose, Calif., USA). Data acquisition and analysis were performed with CellQuest (BD Biosciences, San Jose, Calif., USA). Data was obtained from three independent experiments.

5.2 Results

In view of the direct activation of AMPK by hernandezine and thalidezine, the role of AMPK in hernandezine or thalidezine-mediated cell death in Bax-Bak DKO apoptosis-resistant MEF cells was determined. Apparently, AMPK inhibitor, compound C (CC), significantly suppressed the hernandezine-induced or thalidezine-induced cell death in Bax-Bak DKO apoptosis-resistant MEF cells as shown in FIGS. 7A, 7B, 8A and 8B, confirming the key role of AMPK signaling in these alkaloids-mediated cell death in apoptosis-resistant cells.

Example 6

Abolishing the Hernandezine-Mediated or Thalidezine-Mediated Cell Death in Multidrug-Resistant Cancer Cells by AMPK Inhibitor, Compound C 6.1 Cell Culture and Flow Cytometry Analysis Cell viability was measured using an annexin V staining kit (BD Biosciences, San Jose, Calif., USA). Briefly, HCT-8 taxol resistant colon cancer cells and HCT-116 p53−/− multidrug-resistant colon cancer cells were treated with the 10 µM of hernandezine or 30 µM of thalidezine for 24 h in the presence or absence of AMPK inhibitor, compound C (CC). Cells were then harvested and analyzed by multiparametric flow cytometry using FITC-Annexin V and Propidium iodide staining (BD Biosciences, San Jose, Calif., USA) according to the manufacturer's instructions. Flow cytometry was then carried out using a FACSCalibur flow cytometer (BD Biosciences, San Jose, Calif., USA). Data acquisition and analysis were performed with CellQuest (BD Biosciences, San Jose, Calif., USA). Data was obtained from three independent experiments.

HCT116 p53−/− multidrug-resistant colon cancers are resistant to the following drugs: taxol, etoposide, doxorubicin, cisplatin and staurosporine.

6.2 Results

Figure 9A:
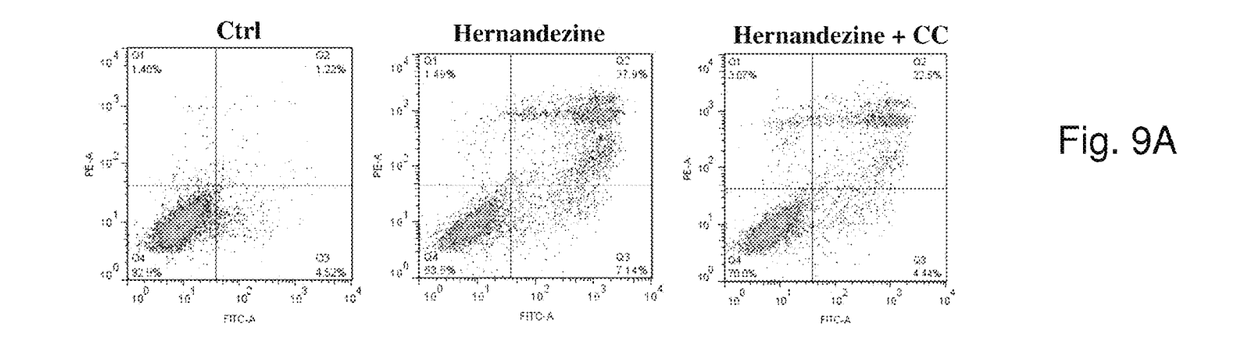
FIG. 9A is the flow cytometry analysis of cell death (annexin V) in response to hernandezine (Her) treatment with or without AMPK inhibitor, compound C (CC), in HCT-8 taxol-resistant colon cancer cells.
Figure 9B:
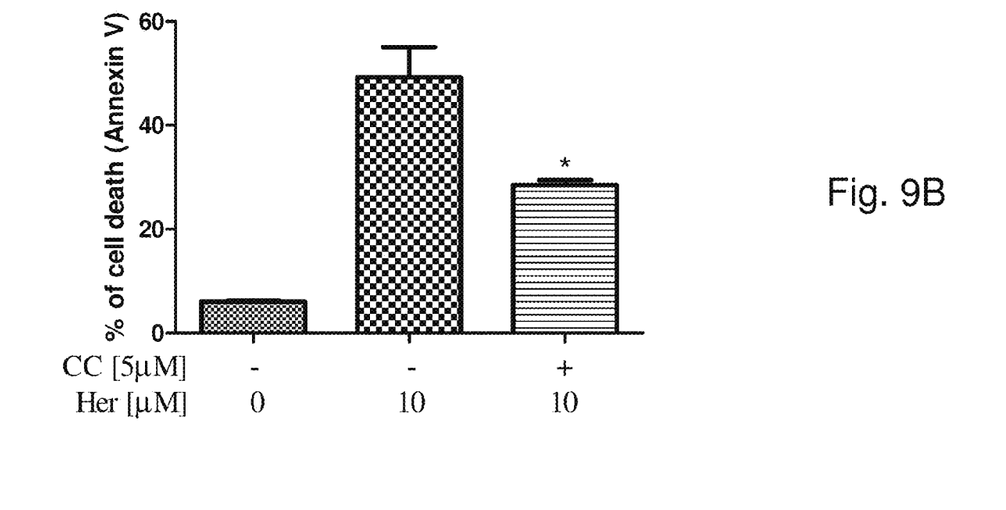
FIG. 9B is the bar chart quantitation for showing the percentage of cell death in response to hernandezine (Her) treatment with or without AMPK inhibitor, compound C (CC), in HCT-8 taxol-resistant colon cancer cells.

First of all, from FIGS. 9A and 9B, it can be shown that hernandezine is able to treat taxol-resistant HCT-8 colon cancers.

Then, apart from HeLa cancer cells, the multidrug-resistant (MDR) cancer cells were also adopted to evaluate the potential anti-cancer effect of hernandezine and thalidezine. For this purpose, taxol-resistant HCT-8 colon cancers were incubated with 10 µM of hernandezine in the presence of CC prior to annexin V flow cytometry analysis. The addition of CC significantly reduced the hernandezine-mediated cell death in these drug-resistant cancers as shown in FIGS. 9A and 9B.

Figure 10A:
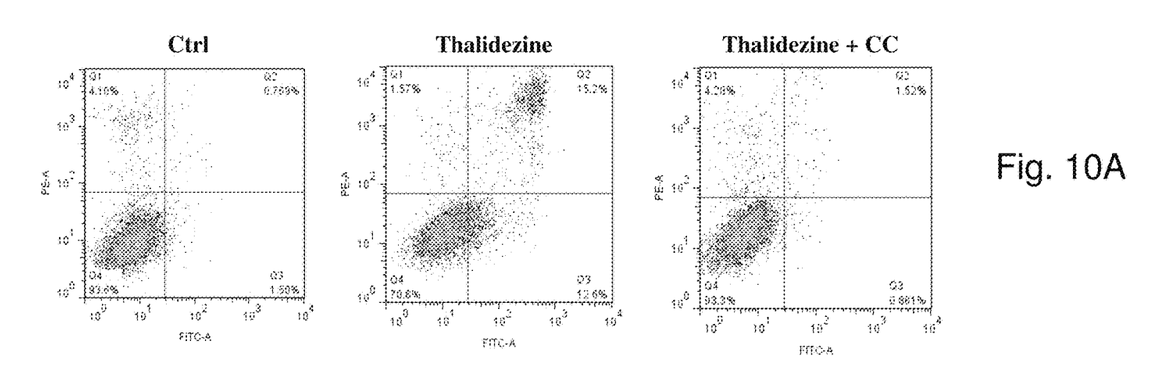
FIG. 10A is the flow cytometry analysis of cell death (annexin V) in response to thalidezine (Tha) treatment with or without AMPK inhibitor, compound C (CC), in HCT-116 p53−/− multidrug-resistant colon cancer cells.
Figure 10B:
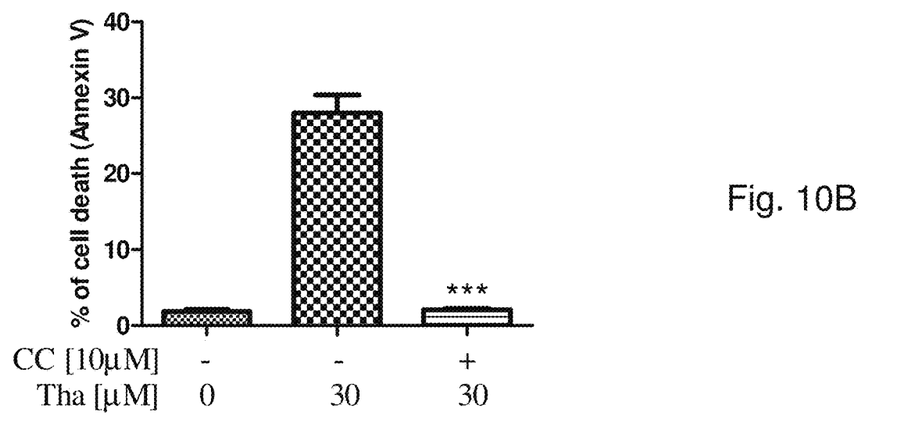
FIG. 10B is the bar chart quantitation for showing the percentage of cell death in response to thalidezine (Tha) treatment with or without AMPK inhibitor, compound C (CC), in HCT-116 p53−/− multidrug-resistant colon cancer cells.

Besides, multidrug-resistant HCT-116 p53 deficient colon cancers were incubated with 30 µM of thalidezine in the presence of CC prior to annexin V flow cytometry analysis. As shown in FIGS. 10A and 10B, thalidezine treatment caused significant cell death in these multidrug-resistant cancers, whereas addition of compound C completely blocked the thalidezine-mediated cell death.

In summary, these two alkaloid compounds, hernandezine and thalidezine, are shown to induce cell death in multidrug-resistant cancer cells via activation of AMPK.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

What is claimed is:

1. A method of treating multidrug-resistant cancer comprising:
   administering an effective amount of thalidezine,
   wherein the multidrug-resistant cancer is p53 deficient multidrug-resistant colon cancer.

2. A method of treating multidrug-resistant cancer comprising:
   administering an effective amount of hernandezine,
   wherein the multidrug-resistant cancer is taxol-resistant colon cancer.

3. The method of claim 1, wherein the multidrug-resistant cancer is resistant to taxol.

4. The method of claim 1, wherein the p53 deficient multidrug-resistant colon cancer is resistant to etoposide.

5. The method of claim 1, wherein the p53 deficient multidrug-resistant colon cancer is resistant to doxorubicin.

6. The method of claim 1, wherein the p53 deficient multidrug-resistant colon cancer is resistant to cisplatin.

7. The method of claim 1, wherein the p53 deficient multidrug-resistant colon cancer is resistant to staurosporine.

8. The method of claim 1 wherein the p53 deficient multidrug-resistant colon cancer is HCT-116 p53 deficient colon cancer.

9. The method of claim 2, wherein the p53 deficient multidrug-resistant colon cancer is HCT-8 colon cancer.

* * * * *